(12) United States Patent
Astier et al.

(10) Patent No.: US 9,977,002 B2
(45) Date of Patent: May 22, 2018

(54) NANOPOROUS STRUCTURES BY REACTIVE ION ETCHING

(71) Applicant: International Business Machines Corporation, Armonk, NY (US)

(72) Inventors: Yann Astier, Irvington, NY (US); Jingwei Bai, Los Angeles, CA (US); Robert L. Bruce, White Plains, NY (US); Aaron D. Franklin, Croton on Hudson, NY (US); Joshua T. Smith, Croton on Hudson, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 352 days.

(21) Appl. No.: 14/734,018

(22) Filed: Jun. 9, 2015

(65) Prior Publication Data

US 2015/0268206 A1 Sep. 24, 2015

Related U.S. Application Data

(62) Division of application No. 13/920,125, filed on Jun. 18, 2013, now Pat. No. 9,117,652.

(51) Int. Cl.
*B32B 5/18* (2006.01)
*G01N 33/00* (2006.01)
(Continued)

(52) U.S. Cl.
CPC ............ *G01N 33/005* (2013.01); *C22C 1/08* (2013.01); *C22C 5/02* (2013.01); *C22C 5/04* (2013.01);
(Continued)

(58) Field of Classification Search
CPC ......... B82B 3/008; B82Y 15/00; B82Y 40/00; C22C 14/00; C22C 1/08; C22C 28/00; C22C 5/02; C22C 5/04; C23F 4/00; G01N 27/414; G01N 33/005; H01L 21/02; Y10S 977/762; Y10S 977/888; Y10T 428/12479
See application file for complete search history.

(56) References Cited

U.S. PATENT DOCUMENTS

| 4,802,951 A | 2/1989 | Clark et al. |
| 4,844,778 A | 7/1989 | Witte |

(Continued)

FOREIGN PATENT DOCUMENTS

| CN | 101717972 B | 11/2011 |
| CN | 101291874 B | 9/2012 |

(Continued)

OTHER PUBLICATIONS

Ji et al., Applied Physics Letters, 2002, 81 (23), pp. 4437-4439.*

(Continued)

*Primary Examiner* — David Sample
*Assistant Examiner* — Elizabeth Collister
(74) *Attorney, Agent, or Firm* — Scully Scott Murphy and Presser; Frank DiGiglio

(57) ABSTRACT

A metal structure including a first metal end region, a second metal end region, and an intermediate region between the first metal end region and the second metal end region, wherein the intermediate region comprises a metal nanostructure having a plurality of pores.

18 Claims, 4 Drawing Sheets

(51) Int. Cl.
*C23F 4/00* (2006.01)
*G01N 27/414* (2006.01)
*H01L 21/02* (2006.01)
*C22C 1/08* (2006.01)
*C22C 5/02* (2006.01)
*C22C 5/04* (2006.01)
*C22C 14/00* (2006.01)
*C22C 28/00* (2006.01)
*B82B 3/00* (2006.01)
*B82Y 15/00* (2011.01)
*B82Y 40/00* (2011.01)

(52) U.S. Cl.
CPC .............. *C22C 14/00* (2013.01); *C22C 28/00* (2013.01); *C23F 4/00* (2013.01); *G01N 27/414* (2013.01); *H01L 21/02* (2013.01); *B82B 3/008* (2013.01); *B82Y 15/00* (2013.01); *B82Y 40/00* (2013.01); *Y10S 977/762* (2013.01); *Y10S 977/888* (2013.01); *Y10T 428/12479* (2015.01)

(56) References Cited

U.S. PATENT DOCUMENTS

| | | | |
|---|---|---|---|
| 5,753,014 A * | 5/1998 | Van Rijn | B01D 39/1692 55/524 |
| 5,843,289 A | 12/1998 | Lee et al. | |
| 6,077,450 A | 6/2000 | Lee | |
| 6,503,382 B1 * | 1/2003 | Bartlett | C25D 9/00 204/483 |
| 2003/0079999 A1* | 5/2003 | Penner | B82Y 15/00 205/775 |
| 2007/0039170 A1 | 2/2007 | Rao et al. | |
| 2010/0269569 A1 | 10/2010 | Yang et al. | |
| 2010/0303722 A1 | 12/2010 | Jin et al. | |
| 2011/0266521 A1 | 11/2011 | Ferrari et al. | |
| 2012/0085145 A1 | 4/2012 | Xiao | |
| 2013/0052475 A1 | 2/2013 | Kim et al. | |
| 2014/0370326 A1 | 12/2014 | Astier et al. | |

FOREIGN PATENT DOCUMENTS

| | | |
|---|---|---|
| CN | 102787445 A | 11/2012 |
| JP | 1072201 A | 3/1989 |
| KR | 1020090093098 A | 9/2009 |
| KR | 100961994 B1 | 6/2010 |
| WO | 2008066965 A2 | 6/2008 |
| WO | 2009125507 A1 | 10/2009 |
| WO | 2012109389 A2 | 8/2012 |

OTHER PUBLICATIONS

Du et al., Applied Materials & interfaces, 2011, 3, pp. 105-109.*
Yang et al., ACS Nano, 2010, 4 (9), pp. 5233-5243.*
D. Lee et al., Scipta Materialia, 2007, 56, pp. 437-440.*
Li et al., Scripta Materlia, 2010, 62, pp. 167-169.*
Zhang et al., Royal Society of Chemistry Chemmical Communications, 2009, pp. 195-197).*
Favier et al., Science, 2001, 293, pp. 227-2231.*
Ding et al., Journal of Chemican Chemical Scoiety, 2003, 125, pp. 7772-7773.*
Kang et al., Chem. Mater., 2000, 12, pp. 3530-3532.*
Antler, Morton, Platinum Metals Rev., 1982, 26 (3), pp. 106-117.*
Liu et al., Journal of Physical Chemistry B, 2006, 110 (9), pp. 4318-4322.*
Cappillino et al., "Nanoporous Pd alloys with compositionally tunable hydrogen storage properties prepared by nanoparticle consolidation", J. Mater. Chem., 2012, vol. 22, pp. 14013-14022.
Campesi et al., "Hydrogen storage properties of Pd nanoparticle/carbon template composites", Carbon, vol. 46, (2008), pp. 206-214.

* cited by examiner

NANOPOROUS STRUCTURES BY REACTIVE ION ETCHING

BACKGROUND

The present invention generally relates to nanoporous structures, and particularly to forming porous nanoscale metal structures by reactive ion etching.

Nanoscale (i.e., less than 100 μm) structures ("Nanostructures") are increasingly having applications in numerous fields, such as metal-ion batteries, energy storage and chemical sensors. One such application is the use of palladium nanowires as hydrogen ($H_2$) sensors. Palladium (Pd) is capable of absorbing hydrogen to form a palladium hydride ($PdH_x$, $0.0<x<\sim0.67$). Because the resistance of the palladium increases as hydrogen absorption increase, a Pd nanowire may be used to sense hydrogen by measuring the conductance across the Pd nanowire. A decrease in conductance may be correlated with an increase of hydrogen concentration in the region around the nanowire.

Nanostructures such as nanowires are particularly useful as chemical sensors due to their high surface-to-volume ratio. For example, because a palladium structure with a high surface-to-volume ratio can more easily absorb hydrogen, it may be more sensitive to environmental changes relative to non-nanoscale structures with lower surface-to-volume ratio. Because there is a correlation between surface-to-volume ratio and sensor performance, it follows that it may be advantageous to further increase the surface-to-volume ratio of palladium nanowires to further increase the sensitivity.

One manner of increasing the surface-to-volume ratio of a nanostructure is to increase it's porosity by forming a plurality of voids in the nanostructure. However, typical processes for forming porous nanostructures require bottom-up manufacturing approaches such as solution phase reactions or dispersion on a surface. Such processes may be difficult to control, scale up, or incorporate into typical fabrication flows. Therefore, a process of forming a porous nanostructure, for example a porous palladium nanowire, using typical semiconductor fabrication processes may be desirable.

SUMMARY

According to one embodiment, a metal structure may be perforated, or made porous, by forming a masking layer above the metal structure, and then removing at least a portion of the masking layer using a reactive ion etching process with an etching gas containing a mask etchant and a metal etchant. While removing the portion of the masking layer, the metal etchant may sputter the metal structure, resulting in the formation of a plurality of pores in the metal structure. In some embodiments, the plurality of pores may have an average diameter of less than 10 nm.

In another embodiment, a porous metal structure may be formed by first forming a metal structure above a substrate. The metal structure may include a first metal end region, a second metal end region, and an intermediate metal region between the first metal end region and the second metal end region. In some embodiments, the intermediate metal region may include a nanostructure or nanostructures, such as a nanowire. A masking layer covering the metal structure may be formed above the metal structure. A protective layer may be formed above the masking layer covering the first metal end region and the second metal end region. The masking layer may then be etched away from above the intermediate metal region using a reactive ion etching process with a mask etchant and a metal etchant. The etching process may form a plurality of pores in the intermediate metal region.

Further embodiments may include a structure comprising a first metal end region, a second metal end region, and an intermediate metal region including a plurality of pores between the first metal end region and the second metal end region. The structure may be made of a metal such as palladium, gold, titanium, or platinum. The intermediate metal region may be a nanostructure such as a nanowire. The plurality of pores may have an average diameter of less than 10 nm, for example 5 nm.

BRIEF DESCRIPTION OF THE DRAWINGS

The following detailed description, given by way of example and not intended to limit the invention solely thereto, will best be appreciated in conjunction with the accompanying drawings, in which.

Figure 1:
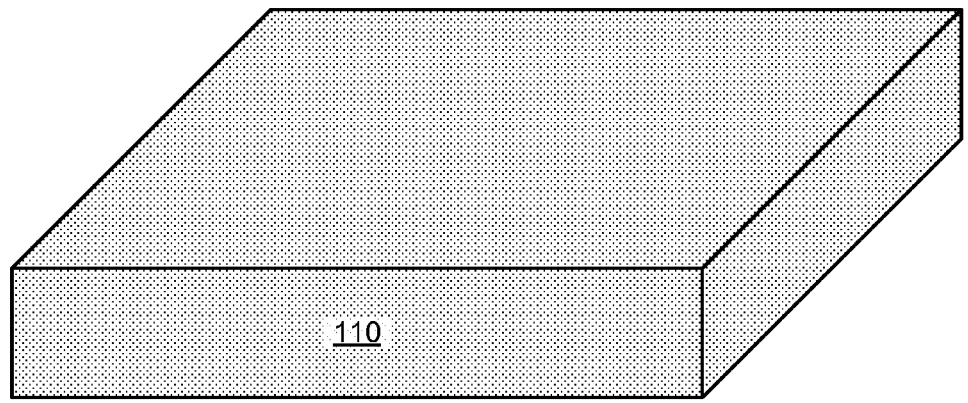
FIG. 1 is an isometric drawing depicting a semiconductor substrate, according to an embodiment of the present invention.

Elements of the figures are not necessarily to scale and are not intended to portray specific parameters of the invention. For clarity and ease of illustration, scale of elements may be exaggerated. The detailed description should be consulted for accurate dimensions. The drawings are intended to depict only typical embodiments of the invention, and therefore should not be considered as limiting the scope of the invention. In the drawings, like numbering represents like elements.

DETAILED DESCRIPTION

Exemplary embodiments will now be described more fully herein with reference to the accompanying drawings, in which exemplary embodiments are shown. This disclosure may, however, be embodied in many different forms and should not be construed as limited to the exemplary embodiments set forth herein. Rather, these exemplary embodiments are provided so that this disclosure will be thorough and complete and will fully convey the scope of this disclosure to those skilled in the art. In the description, details of well-known features and techniques may be omitted to avoid unnecessarily obscuring the presented embodiments.

Embodiments of the invention generally relate to methods of forming a porous metal structure using reactive ion etching. In the embodiments depicted in FIGS. 1-7, the metal structure may include a palladium nanowire connecting two metal pads on each end of the nanowire. Such a structure may be useful, among other things, as a hydrogen sensor, where the nanowire absorbs hydrogen and changes resistance as a result. By perforating the nanowire (i.e., by forming a plurality of pores in the nanowire), the surface area of the nanowire may increase, potentially resulting in an increased ability to absorb hydrogen and improved performance as a sensor. However, embodiments of the present invention are not limited to only nanowires, and the applications of a porous metal structure may extend beyond chemical sensors. After reading the specification, it will be apparent to one of ordinary skill in the art how embodiments further include a large number of porous metal structures, of both nanoscale and larger.

Referring to FIG. 1, a substrate 110 may be provided. The substrate 110 may be made of any material or materials capable of supporting the metal structure described below in conjunction with FIGS. 2-3 and capable of substantially withstanding the etching processes described below in conjunction with FIGS. 6-7. In some embodiments, the substrate 110 may be made of an insulating material such as glass. In other embodiments, the substrate 110 may be made of a semiconductor material such as silicon, germanium, silicon-germanium alloy, silicon carbide, silicon-germanium carbide alloy, and compound (e.g. III-V and II-VI) semiconductor materials. Non-limiting examples of compound semiconductor materials include gallium arsenide, indium arsenide, and indium phosphide.

Typically the substrate 110 may be about, but is not limited to, several hundred microns thick. For example, the substrate 110 may include a thickness ranging from approximately 0.5 mm to approximately 1.5 mm. In some embodiments, the substrate 110 may contain multiple layers of different materials and may contain various microelectronic or nanoscale structures, which have been omitted from the drawings for illustrative clarity.

Figure 2:
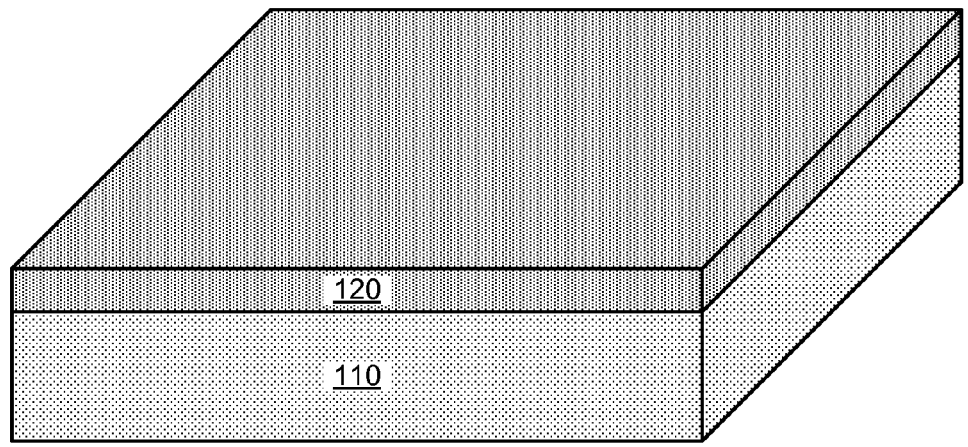
FIG. 2 is an isometric drawing depicting forming a metal layer above the semiconductor substrate, according to an embodiment of the present invention.
Figure 3:
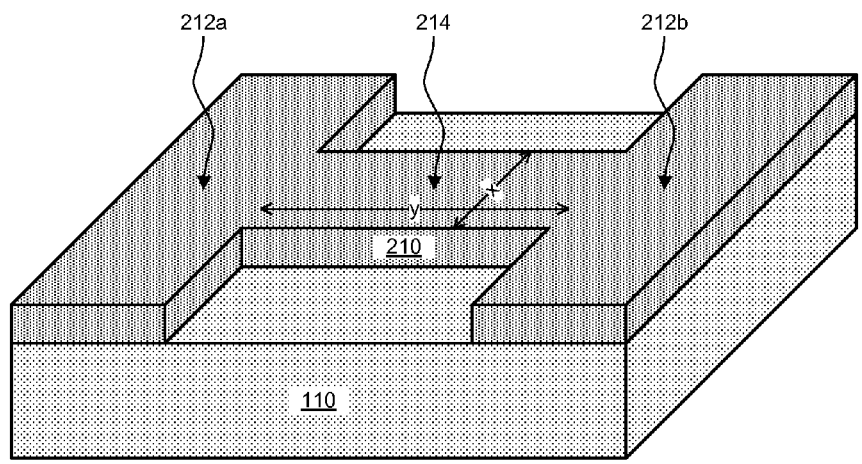
FIG. 3 is an isometric drawing depicting forming a metal structure from the metal layer, according to an embodiment of the present invention.

FIGS. 2-3 depict forming a metal structure 210 (FIG. 3) above the substrate 110. In the depicted embodiment, the metal structure 210 is formed by depositing a metal layer 120 above the substrate 110 and etching the metal layer 120 using typical photolithographic processes. However, the metal structure 210 may also be formed by any other processes known in the art including, for example, a lift-off process, where a pattern may be first formed in a sacrificial layer and the pattern filled with metal before removing the sacrificial layer. A person of ordinary skill in the art will understand how to adapt the method described below to accommodate other methods of forming the metal structure 210.

Referring to FIG. 2, a metal layer 120 may be deposited above the substrate 110. The metal layer 120 may be made of a metal such as palladium, gold, titanium, or platinum. In other embodiments, the metal layer 120 may be made of a metal alloy, such as palladium-nickel or palladium-cerium. Depending on the deposition process used, the metal layer 120 may be as thin as a few angstroms. While there is no upper bound on the thickness of the metal layer 120, the process described below in conjunction with FIGS. 4-6 to perforate portions of the metal layer 120 may result only in pitting of the metal layer 120 rather than holes extending through the metal layer 120. In an exemplary embodiment, the metal layer 120 is a layer of palladium with a thickness of approximately 20 nm.

With continued reference to FIG. 2, the metal layer 120 may be formed using typical metal deposition methods including, but not limited to, sputtering and evaporation. In some embodiments, a seed layer (not shown) made of, for example, titanium, may be deposited between the metal layer 120 and the substrate 110 to improve adhesion of the metal layer 120 to the substrate 110. In some embodiments, the seed layer may have a thickness of approximately 1 nm.

Referring to FIG. 3, a metal structure 210 may be formed from using the metal layer 120. In an exemplary embodiment, the metal structure 210 may be formed using a typical masking and etching process, such as defining the boundaries of the metal structure 210 using a photolithographic layer and then using a RIE process to remove unwanted material from the metal layer 120. In an exemplary embodiment where the metal layer 120 is made of palladium, the RIE process may use argon as an etchant to remove material from the metal layer 120. In some embodiments, a hard mask layer, such as a bi-layer of tantalum and silicon oxide, may be used to prevent overetching of the metal layer 120. In such embodiments, any hard mask layer may be removed after forming the metal structure 210.

With continued reference to FIG. 3, the metal structure may include a first end 212a, a second end 212b, and an intermediate portion 214 between, and joined to, the first end 212a and the second end 212b. In some embodiments, including the embodiment depicted in FIG. 3, the intermediate portion 214 may be a nanostructure such as a nanowire. In embodiments where the intermediate portion 214 is a nanowire, the intermediate portion 214 may have a width x, where x is less than approximately 100 nm. The minimum width x of the intermediate portion 214 may be determined by the method used to form the metal structure 210. Typically, the width x may range from approximately 15 nm to approximately 20 nm.

In other embodiments, the intermediate portion 214 may include metal regions of other shapes and sizes. For example, intermediate portion 214 may include a nanowire having a fan-out structure, where the ends of the nanowire are wider than the middle of the nanowire to reduce contact resistance. In further examples, the intermediate portion 214 may be a metal region of the same width as the first end 212a and the second end 212b, or may be multiple nanowires or fins spanning from the first end 212a to the second end 212b.

In other embodiments, the metal structure 210 may be a single metal layer not including a first end or a second end. In such embodiments, the entire metal structure 210 may be made porous by the etching process described below in conjunction with FIGS. 4-7, excluding the step of forming protective layers over portions of the metal structure 210.

Figure 4:
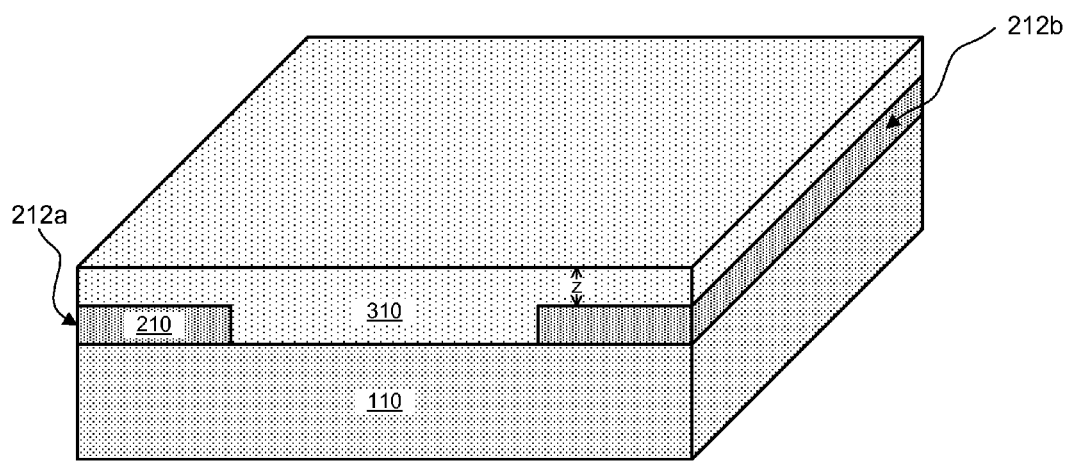
FIG. 4 is an isometric drawing depicting forming a first masking layer above the metal structure, according to an embodiment of the present invention.

Referring to FIG. 4, a masking layer 310 may be formed so that the masking layer 310 covers the metal structure 210. The masking layer 310 may be made of any material which may be etched selectively relative to the material of the metal structure 210. In embodiments where the metal structure 210 is made of palladium, the masking layer 310 may be made of a nitride, such as titanium nitride, silicon nitride, or tantalum nitride, or an oxide such as silicon oxide.

With continued reference to FIG. 4, the masking layer 310 may have a thickness sufficient to just cover the metal structure 210. In an exemplary embodiment, the masking layer 310 may have a thickness z above the top surface of the metal structure 210. In an exemplary embodiment, z may be less than 5 nm, though greater thicknesses are explicitly contemplated.

Figure 5:
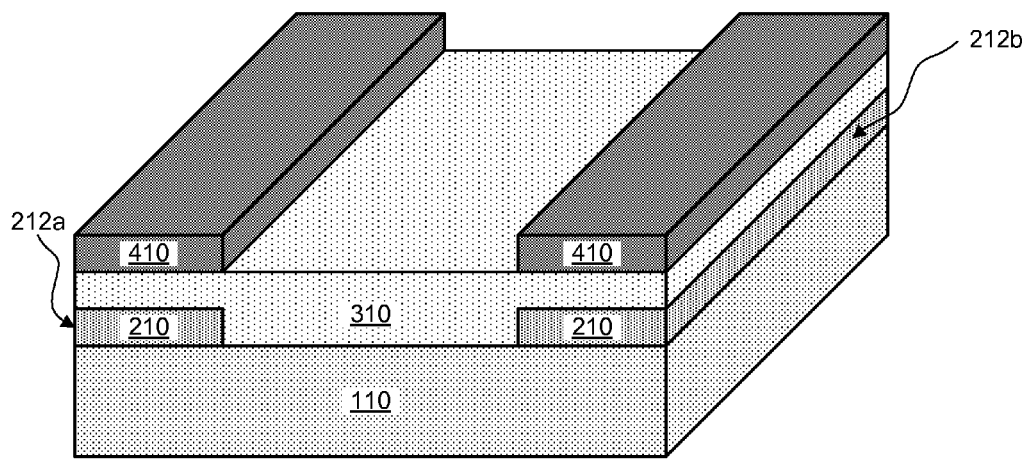
FIG. 5 is an isometric drawing depicting forming a second masking layer above the first masking layer, according to an embodiment of the present invention.

Referring to FIG. 5, protective layers 410 may be formed above the masking 310 over the first end 212a and the second end 212b of the metal structure 210. The protective layers 410 may be made of any suitable material capable of withstanding the etching process described below in conjunction with FIG. 6, so that the first end 212a and the second end 212b are protected while etching the intermediate portion 214. In an exemplary embodiment, the protective layers 410 may be made of a photoresist material.

In some embodiments, the protective layers 410 may include a hard mask layer, such as silicon oxide or silicon nitride, in addition to, or in lieu of, the photoresist material, to increase the durability of the protective layers 410. The material of the protective layers 410 may be selected so that the protective layers 410 may later be selectively removed without removing any of the metal structure 210.

Figure 6:
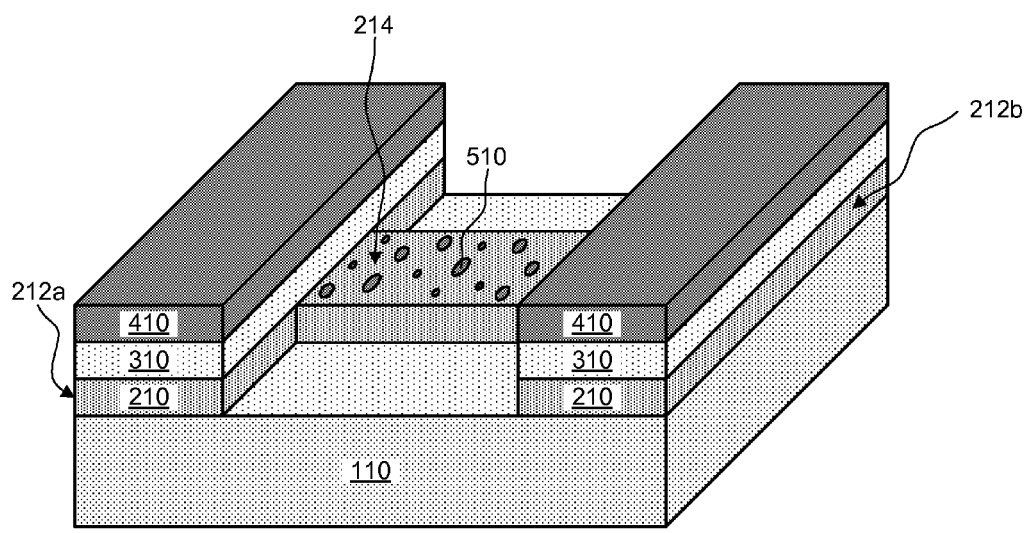
FIG. 6 is an isometric drawing depicting etching the first masking layer and the metal structure, according to an embodiment of the present invention.

Referring to FIG. 6, the masking layer 310 may be etched to expose the intermediate portion 214 of the metal structure 210. The masking layer 310 may be etched with a reactive ion etching process using an etchant gas including a fluorocarbon mask etchant and a metal etchant. In embodiments where the masking layer 310 is made of titanium nitride and the metal structure 210 is made of palladium, the fluorocarbon mask etchant may include chlorine ($Cl_2$) and fluoroform ($CHF_3$) and the metal etchant may include argon (Ar). Alternative dry metal etchants for palladium may include methane ($CH_4$). Etchants for other masking layer materials and metal structure materials are known in the art. The fluorocarbon mask etchant may cause non-uniform etching of the masking layer 310 by fluoride carbon re-deposition. While the mask etchant etches away the masking layer 310, the metal etchant may sputter away portions of the metal structure 210 and transfer the non-uniform etch pattern of the masking layer 310 to the metal structure 210. This uneven etching may result in the formation of a plurality of pores 510 within the intermediate portion 214.

In an exemplary embodiment, the etch process may occur in two stages. In the first stage, the reactive ion etching process chamber may be set at approximately 1000 Watts (W) source power, approximately 250 Watts (W) bias power, and approximately 8 millitorr (mT) pressure and have etchant flow rates of approximately 100 standard cubic centimeters per minute (sccm) Ar, 35 sccm $Cl_2$, and 10 sccm $CHF_3$. In the second stage, the reactive ion etching process chamber may be set at approximately 500 W source power, approximately 20 W bias power, and approximately 8 millitorr (mT) pressure and have etchant flow rates of approximately 100 standard cubic centimeters per minute (sccm) Ar and 35 sccm $Cl_2$. In embodiments where a two step process is used, the amount of the mask etchant may be reduced, so that the rate of the metal sputtering is increased relative to the etch rate of the masking layer 310.

Figure 7:
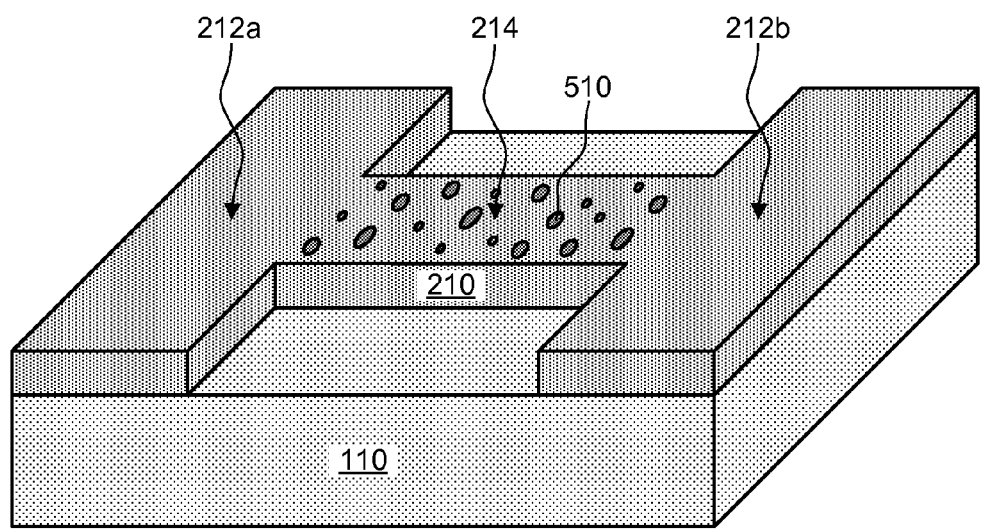
FIG. 7 is an isometric drawing depicting the metal structure having a first end region, a second end region, and a porous middle region between the first end region and the second end region, according to an embodiment of the present invention.

Referring to FIG. 7, the protective layers 410 and any remaining portions of the masking layer 310 may be removed to expose the metal structure 210. In some embodiments, the remaining portions of the masking layer 310 may be left in place. In such embodiments, the remaining portions of the masking layer 310 may serve as contact pads for probing the electrical current through the intermediate portion 214 of the metal structure 210.

The protective layers 410 and any remaining portions of the masking layer 310 may be removed using typical etch processes, either wet or dry, that are suitable for the specific materials used. For example, where the masking layer 310 is made of titanium nitride, the remaining portions of the masking layer 310 may be removed using a wet etch of hydrogen chloride and hydrogen peroxide, or a wet etch of ammonium hydroxide and hydrogen peroxide.

With continued reference to FIG. 7, after removing protective layers 410 and the remaining portions of the masking layer 310, the metal structure 210 remains on the substrate 110. The intermediate portion 214 of the metal structure 210 is perforated by the plurality of pores 510, while the first end 212a and the second end 212b are not porous. The plurality of pores 510 may not be uniform in size. The plurality of pores 510 may also be randomly distributed across the intermediate portion 214. Depending on the specific etch conditions, the plurality of pores 510 may have a maximum diameter of approximately 10 nm, though greater diameters are explicitly contemplated. In some embodiments, the average diameter of the plurality of pores 510 may be approximately 5 nm. The plurality of pores 510 may extend fully through the metal structure 210 in the intermediate portion 214. In other embodiments, at least some of the plurality of pores 510 may extend only partially into the metal structure 210, so that the intermediate portion 214 is only pitted rather than being fully porous.

Once the protective layers 410 and the remaining portions of the masking layer 310 are removed as desired, the structure may continue to undergo typical microelectronic fabrication processes to form desired structures such as chemical sensors. Where the metal structure 210 is used to form part of a chemical sensor, such fabrication processes may include forming electrical contacts to the first end 212a and the second end 212b, so that the resistance of the intermediate portion 214 may be measured. Because the method of forming the porous metal structure 210 described above uses typical semiconductor fabrication processes such as metal deposition, photolithography, and reactive ion etching, it may be more easily incorporated into a microelectronic process flow than methods of forming nanostructures that require a bottom-up approach, such as solution-phase reactions or surface dispersion.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiment, the practical application or technical improvement over technologies found in the marketplace, or to enable other of ordinary skill in the art to understand the embodiments disclosed herein. It is therefore intended that the present invention not be limited to the exact forms and details described and illustrated but fall within the scope of the appended claims.

What is claimed is:

1. A metal structure comprising:
   a first non-porous metal end region;
   a second non-porous metal end region; and
   an intermediate region between the first non-porous metal end region and the second non-porous metal end region, wherein the first non-porous metal end region, the second non-porous metal end region and the intermediate region have co-planar top surfaces and comprise the same metal, and the intermediate region comprises a metal nanostructure having a plurality of pores having an average diameter of less than approximately 10 nm.

2. The structure of claim 1, wherein the plurality of pores fully penetrate the metal nanostructure.

3. The structure of claim 1, wherein the plurality of pores have an average diameter of approximately 5 nm.

4. The structure of claim 1, wherein the first metal end region, the second metal end region, and the intermediate region comprises palladium, gold, titanium, or platinum.

5. The structure of claim 1, wherein the first metal end region, the second metal end region, and the intermediate region comprises palladium-nickel or palladium-cerium.

6. A sensor structure comprising:
a nanowire and two non-porous metal pads above a substrate, wherein the nanowire and the non-porous metal pads comprise the same metal, the nanowire is in direct contact with and extends between the two non-porous metal pads, the nanowire comprises a metal nanostructure having a plurality of pores, and a top surface of the nanowire is co-planar with a top surface of each of the two non-porous metal pads.

7. The structure of claim 6, wherein at least some of the plurality of pores extend fully through an entire thickness of the nanowire.

8. The structure of claim 6, wherein the plurality of pores are non-uniform in size and randomly distributed throughout the metal nanostructure.

9. The structure of claim 6, wherein the plurality of pores have an average diameter of less than approximately 10 nm.

10. The structure of claim 6, wherein nanowire and the two metal pads comprise palladium, gold, titanium, or platinum.

11. The structure of claim 6, wherein nanowire and the two metal pads comprise palladium-nickel or palladium-cerium.

12. A structure comprising:
a metal layer above a semiconductor substrate, the metal layer comprising a non-porous first region, a non-porous second region, and an intermediate region separating the first region from the second region, wherein the first region, the second region and the intermediate region comprise the same metal and have mutually-coplanar top surfaces, and the intermediate region comprises a metal nanowire having a plurality of pores.

13. The structure of claim 12, wherein at least some of the plurality of pores extend fully through an entire thickness of the metal layer in the intermediate region.

14. The structure of claim 12, wherein the plurality of pores have an average diameter of less than approximately 10 nm.

15. The structure of claim 12, wherein the first region, the second region, and the intermediate region comprises palladium, gold, titanium, or platinum.

16. The structure of claim 12, wherein the first region, the second region, and the intermediate region comprise palladium-nickel or palladium-cerium.

17. The structure of claim 12, wherein the intermediate region comprises a nanowire having end portions wider than a middle portion.

18. The structure of claim 12, wherein the intermediate region comprises multiple nanowires extending between the first region and the second region.

* * * * *